United States Patent
Lupia et al.

(10) Patent No.: US 12,303,469 B2
(45) Date of Patent: *May 20, 2025

(54) CANNABIDIOL AND ACTIVE DELIVERY SYSTEMS

(71) Applicant: ELEMENTIS SPECIALTIES, INC., East Windsor, NJ (US)

(72) Inventors: Joseph Anthony Lupia, Chesterfield, NJ (US); Kimberly Burch, Chesterfield, NJ (US); Wouter Ijdo, Yardley, PA (US)

(73) Assignee: ELEMENTIS SPECIALTIES, INC., East Windsor, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/650,432

(22) Filed: Apr. 30, 2024

(65) Prior Publication Data

US 2024/0277628 A1    Aug. 22, 2024

Related U.S. Application Data

(62) Division of application No. 17/324,720, filed on May 19, 2021, now Pat. No. 11,998,514.

(60) Provisional application No. 63/158,008, filed on Mar. 8, 2021, provisional application No. 63/028,020, filed on May 21, 2020.

(51) Int. Cl.

| | |
|---|---|
| *A61K 9/107* | (2006.01) |
| *A61K 9/06* | (2006.01) |
| *A61K 31/05* | (2006.01) |
| *A61K 31/07* | (2006.01) |
| *A61K 31/355* | (2006.01) |
| *A61K 31/375* | (2006.01) |
| *A61K 31/593* | (2006.01) |
| *A61K 36/16* | (2006.01) |
| *A61K 36/185* | (2006.01) |
| *A61K 36/258* | (2006.01) |
| *A61K 36/28* | (2006.01) |
| *A61K 36/42* | (2006.01) |
| *A61K 36/53* | (2006.01) |
| *A61K 36/82* | (2006.01) |
| *A61K 36/886* | (2006.01) |
| *A61K 45/06* | (2006.01) |
| *A61K 47/02* | (2006.01) |
| *A61K 47/10* | (2017.01) |
| *A61K 47/18* | (2017.01) |
| *A61K 47/22* | (2006.01) |
| *A61K 47/44* | (2017.01) |

(52) U.S. Cl.
CPC ............ *A61K 31/05* (2013.01); *A61K 9/06* (2013.01); *A61K 9/107* (2013.01); *A61K 31/07* (2013.01); *A61K 31/355* (2013.01); *A61K 31/375* (2013.01); *A61K 31/593* (2013.01); *A61K 36/16* (2013.01); *A61K 36/185* (2013.01); *A61K 36/258* (2013.01); *A61K 36/28* (2013.01); *A61K 36/42* (2013.01); *A61K 36/53* (2013.01); *A61K 36/82* (2013.01); *A61K 36/886* (2013.01); *A61K 45/06* (2013.01); *A61K 47/02* (2013.01); *A61K 47/10* (2013.01); *A61K 47/186* (2013.01); *A61K 47/22* (2013.01); *A61K 47/44* (2013.01)

(58) Field of Classification Search
None
See application file for complete search history.

(56) References Cited

U.S. PATENT DOCUMENTS

| | | |
|---|---|---|
| 10,143,755 B2 | 12/2018 | Borja et al. |
| 2015/0017105 A1 | 1/2015 | Borja |
| 2020/0000721 A1 | 1/2020 | Blake |
| 2020/0108025 A1 | 4/2020 | Ghalili et al. |
| 2021/0121514 A1 | 4/2021 | Williams |

FOREIGN PATENT DOCUMENTS

| | | |
|---|---|---|
| WO | 2010127033 A1 | 11/2010 |
| WO | 2016/007331 A1 | 1/2016 |
| WO | 2021113083 A1 | 6/2021 |

OTHER PUBLICATIONS

Abdullahi S. et al. Characterization of Ashaka and Tango Bentonites Surfaces after Modification . . . J Chemical Society Nigeria 43(1) 140-146, 2018.

Ghadiri M. et al. Biomedical Applications of Cationic Clay Minerals Royal Society of Chemistry 5:29467-29481, 2015.

International Search Report and Written Opinion issued in corresponding International Application No. PCT/US21/33123 mailed Aug. 16, 2021.

*Primary Examiner* — Michael V Meller
(74) *Attorney, Agent, or Firm* — Carol A. Marmo; Eckert Seamans Cherin & Mellott, LLC

(57) ABSTRACT

A cannabidiol (CBD) gelled delivery system comprising: a rheology modifier; an emollient; and one or more cannabidiols selected from the group consisting of a cannabidiol broad spectrum oil, a cannabidiol full spectrum oil, or a cannabidiol isolate. A CBD emulsified delivery system comprising: a rheology modifier; an emollient; a polyglyceryl ester surfactant; and one or more cannabidiols selected from the group consisting of a cannabidiol broad spectrum oil, a cannabidiol full spectrum oil, or a cannabidiol isolate. For such delivery systems, the cannabidiols contain less than 0.3 wt. % of tetrahydrocannabinol (THC) or the cannabidiols are substantially free of THC. An active gelled delivery system a rheology modifier; an emollient; and one or more actives. An active emulsified delivery system comprising: a rheology modifier; an emollient; a polyglyceryl ester surfactant; and one or more actives.

1 Claim, No Drawings

CANNABIDIOL AND ACTIVE DELIVERY SYSTEMS

CROSS-REFERENCE TO RELATED APPLICATIONS

The application is a divisional of U.S. application Ser. No. 17/324,720, filed May 19, 2021 which claims priority benefit from U.S. Provisional Patent Application 63/028,020 filed May 21, 2020 and U.S. Provisional Patent Application 63/158,008 filed Mar. 8, 2021 each of which is incorporated by reference herein in its entirety.

FIELD OF THE DISCLOSURE

The present disclosure provides for various active delivery systems used in topical applications.

SUMMARY OF DISCLOSURE

The present disclosure provides for a cannabidiol (CBD) gelled delivery system comprising 1 wt. % to 20 wt. % of a rheology modifier; 50 wt. % to 90 wt. % of an emollient; and 2 wt. % to 40 wt. % of one or more cannabidiols selected from the group consisting of a cannabidiol broad spectrum oil, a cannabidiol full spectrum oil, or a cannabidiol isolate.

The present disclosure also provided for a cannabidiol (CBD) emulsified delivery system comprising 1 wt. % to 20 wt. % of a rheology modifier; 10 wt. % to 60 wt. % of an emollient; 10 wt. % to 50 wt. % of polyglyceryl ester surfactant; and 2 wt. % to 40 wt. % of one or more cannabidiols selected from the group consisting of a cannabidiol broad spectrum oil, a cannabidiol full spectrum oil, or a cannabidiol isolate.

The present disclosure provides for an active gelled delivery system comprising: 1 wt. % to 20 wt. % of a rheology modifier; 50 wt. % to 90 wt. % of an emollient; and 2 wt. % to 40 wt. % of one or more actives selected from the group consisting of vitamins, retinoid, proteins, amino acids, polypeptides, protein derivatives, biologicals, antioxidants, moisturizers, anti-acne, anti-wrinkle, anti-antropy, antioxidants, conditioning agents, film forming polymers, antiperspirants, deodorants, anti-dandruff, skin protectants and combinations thereof.

The present disclosure also provided for an active emulsified delivery system comprising 1 wt. % to 20 wt. % of a rheology modifier; 10 wt. % to 60 wt. % of an emollient; 10 wt. % to 50 wt. % of polyglyceryl ester surfactant; and 2 wt. % to 40 wt. % of one or more actives selected from the group consisting of vitamins, retinoid, proteins, amino acids, polypeptides, protein derivatives, biologicals, antioxidants, moisturizers, anti-acne, anti-wrinkle, anti-antropy, antioxidants, conditioning agents, film forming polymers, antiperspirants, deodorants, anti-dandruff, skin protectants and combinations thereof.

DETAILED DESCRIPTION OF THE EMBODIMENTS

The present disclosure first provides for various embodiments of CBD delivery systems.

In one embodiment, the present disclosure provides for a CBD gelled delivery system comprising 1 wt. % to 20 wt. % of a rheology modifier; 50 wt. % to 90 wt. % of an emollient; and 2 wt. % to 40 wt. % of one or more cannabidiols selected from the group consisting of a cannabidiol broad spectrum oil, a cannabidiol full spectrum oil, or a cannabidiol isolate.

In certain embodiments, the cannabidiols contain less than 0.3 wt. % of tetrahydrocannabinol (THC) or the cannabidiols are substantially free of THC. Such a gelled delivery system provides thermostable viscosity control of the gelled delivery system's oil phase, improves application properties, enhances skin-feel by masking greasy or tacky components and imparts a pleasant residual silkiness to the skin. The gelled delivery system has shear-thinning rheology resulting in a smooth application to the skin.

For the CBD gelled delivery system, the amounts of rheology modifier, emollient, cannabidiol may vary. The amount of rheology modifier is selected from 1 wt. % to 20 wt. %; 5 wt. % to 20 wt. %; 7 wt. % to 15 wt. %; or 8 wt. % to 10 wt. %. The amount of emollient is selected from 50 wt. % to 90 wt. %; 70 wt. % to 90 wt. %; or 70 wt. % to 80 wt. %. The amount of cannabidiol can vary from 2 wt. % to 40 wt. %; 2 wt. % to 20 wt. %; or 5 wt. % to 10 wt. %. In the various embodiments of the CBD gelled delivery system, the above amounts of rheology modifier, emollient and canabidiol may be combined interchangeably.

In certain embodiments of the CBD gelled delivery system, the rheology modifier is an organoclay, In some such embodiments, the organoclay contains a polar activator at amounts selected from 10 wt. % to 50 wt. %; 20 wt. % to 40 wt. %; or 25 wt. % to 35 wt. % based on the weight of the organoclay. In some embodiments, the polar activator may contain $H_2O$ at amounts selected from 0.01 wt. % to 5 wt. %; or 0.01 wt. % to 10 wt. %. In some embodiments, the polar activator is substantially free of water.

Various organoclays may be used in the CBD gelled delivery system. In certain embodiments, the organoclay is a smectite clay exchanged with a quaternary ammonium cation having a formula of $[N-R^1R^2R^3R^4]^+$ wherein $R^1$ comprises a group selected from (i) linear or branched aliphatic, aralkyl, or aromatic hydrocarbon groups having from 8 to 30 carbon atoms or (ii) alkyl or alkyl-ester groups having 8 to 30 carbon atoms; $R^2$, $R^3$ and $R^4$ are independently selected from the group consisting of (a) linear or branched aliphatic, aralkyl and aromatic groups having from 1 to about 30 carbon atoms. In certain such embodiments, the quaternary ammonium cation is selected from the group consisting of (i) dimethyldialkyl ammonium cation wherein the alkyl hydrocarbon group has 8 to 30 carbon atoms or 12 to 22 carbon atoms; (ii) benzyldimethylalkyl ammonium cation wherein the alkyl hydrocarbon group has 8 to 30 carbon atoms or 12 to 22 carbon atoms, and (iii) combinations thereof.

In certain other embodiments, the organoclay is an organically modified layered double hydroxide. These organically modified layered double hydroxides are comprised of layered double hydroxides and anionic surfactants. Layered double hydroxides (LDH) comprise an class of layered materials with positively charged hydroxide layers and charge balancing, mobile anions located in the interlayer region. The anions in the interlayers of LDHs are exchangeable. A variety of organic anionic surfactants can be intercalated between the hydroxide layers and suitable organic anions having at least 8 carbon atoms include mono-, di- or polycarboxylates, sulfonates, phosphonates, and sulfates. Organic anions in excess of the clay anion exchange capacity may optionally be co-intercalated as salts in the interlayer region. Layered double hydroxides are also known as mixed metal hydroxides and include the group of hydrotalcite materials. The layer charge density and organic surface treatment can be optimized to provide optimal properties with respect to rheological performance and other applications parameters. The disclosures of U.S. Pat. Nos. 7,968, 740, 7,786,202, 6,479,421, 6,365,661, 6,028,023 and 3,539,306 as well as E.P. Patent No. 1,814,822 are each incorporated in their entirety herein.

In certain other embodiments of the CBD gelled delivery system, the rheology modifier is selected from the group consisting of ethylcellulose, dibutyl lauroyl glutamide, dibutyl ethylhexanoyl glutamide, silica dimethyl silylate, hydrogenated styrene/isoprene copolymer, Polyamide-8, ethylene/propylene/styrene copolymer, butylene/ethylene/styrene copolymer, dextrin palmitate, trihydroxystearin and combinations thereof.

In certain embodiments of the CBD gelled delivery system, the emollient is selected from the group consisting of hemisqualane, $C_{9-12}$ alkane, hemp oil, jojoba oil, caprylic/capric triglyceride, coco caprylate/caprate, octyldodecanol, natural oils, including plant oils, vegetable oils, and combinations thereof. In some such embodiments, the natural oil is sourced from plants, fruits, seeds, insects, or animals. In certain embodiments, the natural oil is selected from the group consisting of lanolin, shea butter, cocoa butter, mineral oil, beeswax, carnauba or palm wax, squalene, coconut oil, almond oil, olive oils and sesame oils. In certain embodiments, the natural emollient is an extract comprised largely of long chain waxy esters. It will be appreciated by a person skilled in the art that this list of natural oils is not an exhaustive list, and is representative only.

In yet other embodiments, of the CBD gelled delivery system, the system includes one or more vitamins each selected from the group consisting of vitamin A, vitamin B, vitamin C, vitamin D, vitamin E, and derivatives thereof.

In another embodiment, the present disclosure provides for a CBD emulsified delivery system comprising: 1 wt. % to 20 wt. % of a rheology modifier; 10 wt. % to 60 wt. % of an emollient; 10 wt. % to 50 wt. % of polyglyceryl ester surfactant; and 2 wt. % to 40 wt. % of one or more cannabidiols selected from the group consisting of a cannabidiol broad spectrum oil, a cannabidiol full spectrum oil, or a cannabidiol isolate. In certain embodiments, the cannabidiols contain less than 0.3 wt. % of tetrahydrocannabinol (THC) or the cannabidiols are substantially free of THC. Such an emulsified delivery system provides emulsification and rheology (including suspension) resulting in stable emulsions. The emulsified delivery system creates water in oil emulsions with up to 70% water in the internal phase.

For the CBD emulsified delivery system, the amounts of rheology modifier, emollient, cannabidiol and polyglyceryl ester surfactant may vary. The amount of rheology modifier is selected from 1 wt. % to 20 wt. %; 5 wt. % to 20 wt. %; 7 wt. % to 15 wt. %; or 8 wt. % to 10 wt. %. The amount of emollient is selected from 10 wt. % to 60 wt. %; 30 wt. % to 50 wt. %; or 35 wt. % to 45 wt. %. The amount of cannabidiol can vary from 2 wt. % to 40 wt. %; 2 wt. % to 20 wt. %; or 5 wt. % to 10 wt. %. The amount of polyglyceryl ester surfactant is selected from 10 wt. % to 50 wt. %; 20 wt. % to 40 wt. %; and 30 wt. % to 40 wt. %. In the various embodiments of the CBD emulsified delivery system, the above amounts of rheology modifier, emollient, polyglyceryl ester surfactant and cannabidiol may be combined interchangeably.

In certain embodiments of the CBD emulsified delivery system, the rheology modifier is an organoclay. Various organoclays may be used in the CBD emulsified delivery system. In certain embodiments, the organoclay is a smectite clay exchanged with a quaternary ammonium cation having a formula of $[N-R^1R^2R^3R^4]^+$ wherein $R^1$ comprises a group selected from (i) linear or branched aliphatic, aralkyl, or aromatic hydrocarbon groups having from 8 to 30 carbon atoms or (ii) alkyl or alkyl-ester groups having 8 to 30 carbon atoms; $R^2$, $R^3$ and $R^4$ are independently selected from the group consisting of (a) linear or branched aliphatic, aralkyl and aromatic groups having from 1 to about 30 carbon atoms. In certain such embodiments, the quaternary ammonium cation is selected from the group consisting of (i) dimethyldialkyl ammonium cation wherein the alkyl hydrocarbon group has 8 to 30 carbon atoms or 12 to 22 carbon atoms; (ii) benzyldimethylalkyl ammonium cation wherein the alkyl hydrocarbon group has 8 to 30 carbon atoms or 12 to 22 carbon atoms, and (iii) combinations thereof.

In certain other embodiments, the organoclay is an organically modified layered double hydroxide. These organically modified layered double hydroxides are comprised of layered double hydroxides and anionic surfactants. Layered double hydroxides (LDH) comprise an class of layered materials with positively charged hydroxide layers and charge balancing, mobile anions located in the interlayer region. The anions in the interlayers of LDHs are exchangeable. A variety of organic anionic surfactants can be intercalated between the hydroxide layers and suitable organic anions having at least 8 carbon atoms include mono-, di- or polycarboxylates, sulfonates, phosphonates, and sulfates. Organic anions in excess of the clay anion exchange capacity may optionally be co-intercalated as salts in the interlayer region. Layered double hydroxides are also known as mixed metal hydroxides and include the group of hydrotalcite materials. The layer charge density and organic surface treatment can be optimized to provide optimal properties with respect to rheological performance and other applications parameters. The disclosures of U.S. Pat. Nos. 7,968,740, 7,786,202, 6,479,421, 6,365,661, 6,028,023 and 3,539,306 as well as E.P. Patent No. 1,814,822 are each incorporated in their entirety herein.

In certain other embodiments of the CBD emulsified delivery system, the rheology modifier is selected from the group consisting of ethylcellulose, dibutyl lauroyl glutamide, dibutyl ethylhexanoyl glutamide, silica dimethyl silylate, hydrogenated styrene/isoprene copolymer, Polyamide-8, ethylene/propylene/styrene copolymer, butylene/ethylene/styrene copolymer, dextrin palmitate, trihydroxystearin and combinations thereof.

In certain embodiments of the CBD emulsified delivery system, the emollient is selected from the group consisting of hemisqualane, $C_{9-12}$ alkane, hemp oil, jojoba oil, caprylic/capric triglyceride, coco caprylate/caprate, octyldodecanol, natural oils, including plant oils, vegetable oils, and combinations thereof. In some such embodiments, the natural oil is sourced from plants, fruits, seeds, insects, or animals. In certain embodiments, the natural oil is selected from the group consisting of lanolin, shea butter, cocoa butter, mineral oil, beeswax, carnauba or palm wax, squalene, coconut oil, almond oil, olive oils and sesame oils. In certain embodiments, the natural emollient is an extract comprised largely of long chain waxy esters. It will be appreciated by a person skilled in the art that this list of natural oils is not an exhaustive list, and is representative only.

In yet other embodiments, of the CBD emulsified delivery system, the system includes one or more vitamins each selected from the group consisting of vitamin A, vitamin B, vitamin C, vitamin D, vitamin E, and derivatives thereof.

The present disclosure further provides for embodiments of active delivery systems.

In one embodiment, the present disclosure provides for an active gelled delivery system comprising: 1 wt. % to 20 wt. % of a rheology modifier; 50 wt. % to 90 wt. % of an emollient; and 2 wt. % to 40 wt. % of one or more actives selected from the group consisting of vitamins, retinoid, proteins, amino acids, polypeptides, protein derivatives, biologicals, antioxidants, moisturizers, anti-acne, anti-wrinkle, anti-antropy, antioxidants, conditioning agents, film forming polymers, anti-perspirants, deodorants, anti-dandruff, skin protectants and combinations thereof. Such a gelled delivery system provides thermostable viscosity control of the gelled delivery system's oil phase, improves application properties, enhances skin-feel by masking greasy or tacky components and imparts a pleasant residual silkiness to the skin. The gelled delivery system has shear-thinning rheology resulting in a smooth application to the skin.

For the active gelled delivery system, the amounts of rheology modifier, emollient, active may vary. The amount of rheology modifier is selected from 1 wt. % to 20 wt. %; 5 wt. % to 20 wt. %; 7 wt. % to 15 wt. %; or 8 wt. % to 10 wt. %. The amount of emollient is selected from 50 wt. % to 90 wt. %; 70 wt. % to 90 wt. %; or 70 wt. % to 80 wt. %. The amount of active can vary from 2 wt. % to 40 wt. %; 2 wt. % to 20 wt. %; or 5 wt. % to 10 wt. %. In the various embodiments of the active gelled delivery system, the above amounts of rheology modifier, emollient and active may be combined interchangeably.

In some embodiments, of the active gelled delivery system, the vitamins actives are selected from the group consisting of vitamin A, vitamin B, vitamin C, vitamin D, vitamin E, and derivatives thereof.

In some embodiments, of the active gelled delivery system, the moisturizers are selected from the group consisting of humectants, film formers, occlusive agents, and agents that affect the natural moisturization mechanisms of the skin.

In some embodiments, of the active gelled delivery system, the humectants are selected from the group consisting of sugar and starch derivatives (e.g., alkoxylated glucose); hyaluronic acid, guanidine; glycolic acid and glycolate salts (e.g., ammonium and quaternary alkyl ammonium); lactic acid and lactate salts (e.g., ammonium and quaternary alkyl ammonium).

In some embodiments, of the active gelled delivery system, the skin conditioning agents are selected from the group consisting of aloe extracts, allantoin, bisabolol, ceramides, dimethicone, biosaccharide gum, ethylhexylglycerin, pentylene glycol, hydrogenated polydecene, octyldodecyl oleate, and dipotassium glycyrrhizate.

In some embodiments, of the active gelled delivery system, the film forming polymers are selected from the group consisting of sulfopolyester resins, water dispersible, non-crosslinked acrylic resins, polyvinylacetate/polyvinyl alcohol resins, polyvinyl pyrrolidone (PVP), PVP/VA copolymers and mixtures of said film forming polymers.

In some embodiments, of the active gelled delivery system, the botanicals are selected from the group consisting of aloe vera, chamomile, cucumber extract, *Ginkgo biloba*, *ginseng*, and rosemary white tea extract, green tea extract, *ginseng*, and other natural compounds.

In some embodiments, of the active gelled delivery system, the antioxidants are selected from the group consisting of BHT and tocopherol.

In some embodiments, of the active gelled delivery system, antiperspirant actives may be selected from the group consisting of Aluminumchlorohydrate, Aluminumsesquichlorohydrate, Aluminumdichlorohydrate, Aluminum Zirconium octachlorohydrate, Aluminum Zirconium pentachlorohydrate, Aluminum Zirconium tetrachlorohydrate, Aluminum Zirconium trichlorohydrate as well as glycine and calcium glycine complexes and salts thereof. The disclosures of U.S. Pat. Nos. 9,174,851 and 10,117,814 are each incorporated in their entirety herein.

In some embodiments, of the active gelled delivery system, anti-dandruff actives are selected from the group consisting of coal tar extract, pyritione zinc, salicylic acid, selenium sulfide, ketoconazole, quaternary ammonium compounds. The disclosures of U.S. Pat. Nos. 9,242,002, 9,968,537 and 10,004,678 are each incorporated in their entirety herein.

In some embodiments, of the active gelled delivery system, deodorants are selected from the group consisting of: antimicrobial compounds, adsorbents or absorbent compounds, Zinc oxide, Titanium dioxide, Clay, Bentonite, Charcoal, Baking soda, Fragrance, Perfume, Essential Oils, lavender, peppermint, and tea tree oils, Extracts, Rose, Vanilla, Juniper or Mint extracts. Antimicrobial compounds are described in U.S. Pat. Nos. 6,709,647; 6,503,490; 5,885,562 are each incorporated in their entirety herein.

The various vitamins, moisturizers, skin conditioning agents, film forming polymers, botanicals, antioxidants, anti-perspirants, anti-dandruff and deodorants of the foregoing embodiments of the active gelled delivery systems, may be combined as a particular embodiment of an active gelled delivery system.

In certain embodiments of the active gelled delivery system, the rheology modifier is an organoclay, In some such embodiments, the organoclay contains a polar activator at amounts selected from 10 wt. % to 50 wt. %; 20 wt. % to 40 wt. %; or 25 wt. % to 35 wt. % based on the weight of the organoclay. In some embodiments, the polar activator may contain $H_2O$ at amounts selected from 0.01 wt. % to 5 wt. %; or 0.01 wt. % to 10 wt. %. In some embodiments, the polar activator is substantially free of water.

Various organoclays may be used in the active gelled delivery system. In certain embodiments, the organoclay is a smectite clay exchanged with a quaternary ammonium cation having a formula of $[N-R^1R^2R^3R^4]^+$ wherein wherein $R^1$ comprises a group selected from (i) linear or branched aliphatic, aralkyl, or aromatic hydrocarbon groups having from 8 to 30 carbon atoms or (ii) alkyl or alkyl-ester groups having 8 to 30 carbon atoms; $R^2$, $R^3$ and $R^4$ are independently selected from the group consisting of (a) linear or branched aliphatic, aralkyl and aromatic groups having from 1 to about 30 carbon atoms. In certain such embodiments, the quaternary ammonium cation is selected from the group consisting of (i) dimethyldialkyl ammonium cation wherein the alkyl hydrocarbon group has 8 to 30 carbon atoms or 12 to 22 carbon atoms; (ii) benzyldimethylalkyl ammonium cation wherein the alkyl hydrocarbon group has 8 to 30 carbon atoms or 12 to 22 carbon atoms, and (iii) combinations thereof.

In certain other embodiments, the organoclay is an organically modified layered double hydroxide. These organically modified layered double hydroxides are comprised of layered double hydroxides and anionic surfactants. Layered double hydroxides (LDH) comprise an class of layered materials with positively charged hydroxide layers and charge balancing, mobile anions located in the interlayer region. The anions in the interlayers of LDHs are exchangeable. A variety of organic anionic surfactants can be intercalated between the hydroxide layers and suitable organic anions having at least 8 carbon atoms include mono-, di- or polycarboxylates, sulfonates, phosphonates, and sulfates. Organic anions in excess of the clay anion exchange capacity may optionally be co-intercalated as salts in the interlayer region. Layered double hydroxides are also known as mixed metal hydroxides and include the group of hydrotalcite materials. The layer charge density and organic surface treatment can be optimized to provide optimal properties with respect to rheological performance and other applications parameters. The disclosures of U.S. Pat. Nos. 7,968,740, 7,786,202, 6,479,421, 6,365,661, 6,028,023 and 3,539,306 as well as E.P. Patent No. 1,814,822 are each incorporated in their entirety herein.

In certain other embodiments of the active gelled delivery system, the rheology modifier is selected from the group consisting of ethylcellulose, dibutyl lauroyl glutamide, dibutyl ethylhexanoyl glutamide, silica dimethyl silylate, hydrogenated styrene/isoprene copolymer, Polyamide-8, ethylene/propylene/styrene copolymer, butylene/ethylene/styrene copolymer, dextrin palmitate, trihydroxystearin and combinations thereof.

In certain embodiments of the active gelled delivery system, the emollient is selected from the group consisting of hemisqualane, $C_{9-12}$ alkane, hemp oil, jojoba oil, caprylic/capric triglyceride, coco caprylate/caprate, octyldodecanol, natural oils, including plant oils, vegetable oils, and combinations thereof. In some such embodiments, the natural oil is sourced from plants, fruits, seeds, insects, or animals. In certain embodiments, the natural oil is selected from the group consisting of lanolin, shea butter, cocoa butter, mineral oil, beeswax, carnauba or palm wax, squalene, coconut oil, almond oil, olive oils and sesame oils. In certain embodiments, the natural emollient is an extract comprised largely of long chain waxy esters. It will be appreciated by a person skilled in the art that this list of natural oils is not an exhaustive list, and is representative only.

In another embodiment, the present disclosure provides for an active emulsified delivery system comprising: 1 wt. % to 20 wt. % of a rheology modifier; 10 wt. % to 60 wt. % of an emollient; 10 wt. % to 50 wt. % of polyglyceryl ester surfactant; and 2 wt. % to 40 wt. % of one or more actives selected from the group consisting of vitamins, retinoid, proteins, amino acids, polypeptides, protein derivatives, biologicals, antioxidants, moisturizers, anti-acne, anti-wrinkle, anti-antropy, antioxidants, conditioning agents, film forming polymers, anti-perspirants, deodorants, anti-dandruff, skin protectants and combinations thereof. The active emulsified delivery system creates water in oil emulsions with up to 70% water in the internal phase For the active emulsified delivery system, the amounts of rheology modifier, emollient, active and polyglyceryl ester surfactant may vary. The amount of rheology modifier is selected from 1 wt. % to 20 wt. %; 5 wt. % to 20 wt. %; 7 wt. % to 15 wt. %; or 8 wt. % to 10 wt. %. The amount of emollient is selected from 10 wt. % to 60 wt. %; 30 wt. % to 50 wt. %; or 35 wt. % to 45 wt. %. The amount of active can vary from 2 wt. % to 40 wt. %; 2 wt. % to 20 wt. %; or 5 wt. % to 10 wt. %. The amount of polyglyceryl ester surfactant is selected from 10 wt. % to 50 wt. %; 20 wt. % to 40 wt. %; and 30 wt. % to 40 wt. % In the various embodiments of the active emulsified delivery system, the above amounts of rheology modifier, emollient, polyglyceryl ester surfactant and active may be combined interchangeably.

In some embodiments, of the active emulsified delivery system, the vitamins actives are selected from the group consisting of vitamin A, vitamin B, vitamin C, vitamin D, vitamin E, and derivatives thereof.

In some embodiments, of the active emulsified delivery system, the moisturizers are selected from the group consisting of humectants, film formers, occlusive agents, and agents that affect the natural moisturization mechanisms of the skin.

In some embodiments, of the active emulsified delivery system, the humectants are selected from the group consisting of sugar and starch derivatives (e.g., alkoxylated glucose); hyaluronic acid, guanidine; glycolic acid and glycolate salts (e.g., ammonium and quaternary alkyl ammonium); lactic acid and lactate salts (e.g., ammonium and quaternary alkyl ammonium).

In some embodiments, of the active emulsified delivery system, the skin conditioning agents are selected from the group consisting of aloe extracts, allantoin, bisabolol, ceramides, dimethicone, biosaccharide gum, ethylhexylglycerin, pentylene glycol, hydrogenated polydecene, octyldodecyl oleate, and dipotassium glycyrrhizate.

In some embodiments, of the active emulsified delivery system, the film forming polymers are selected from the group consisting of sulfopolyester resins, water dispersible, non-crosslinked acrylic resins, polyvinylacetate/polyvinyl alcohol resins, polyvinyl pyrrolidone (PVP), PVP/VA copolymers and mixtures of said film forming polymers.

In some embodiments, of the active emulsified delivery system, the botanicals are selected from the group consisting of aloe vera, chamomile, cucumber extract, *Ginkgo biloba, ginseng*, and rosemary white tea extract, green tea extract, *ginseng*, and other natural compounds.

In some embodiments, of the active emulsified delivery system, the antioxidants are selected from the group consisting of BHT and tocopherol.

In some embodiments, of the active emulsified delivery system, antiperspirant actives may be selected from the group consisting of Aluminumchlorohydrate, Aluminumsesquichlorohydrate, Aluminumdichlorohydrate, Aluminum Zirconium octachlorohydrate, Aluminum Zirconium pentachlorohydrate, Aluminum Zirconium tetrachlorohydrate, Aluminum Zirconium trichlorohydrate as well as glycine and calcium glycine complexes and salts thereof. The disclosures of U.S. Pat. Nos. 9,174,851 and 10,117,814 are each incorporated in their entirety herein.

In some embodiments, of the active emulsified delivery system, anti-dandruff actives are selected from the group consisting of coal tar extract, pyritione zinc, salicylic acid, selenium sulfide, ketoconazole, quaternary ammonium compounds. The disclosures of U.S. Pat. Nos. 9,242,002, 9,968,537 and 10,004,678 are each incorporated in their entirety herein.

In some embodiments, of the active emulsified delivery system, deodorants are selected from the group consisting of: antimicrobial compounds, adsorbents or absorbent compounds, Zinc oxide, Titanium dioxide, Clay, Bentonite, Charcoal, Baking soda, Fragrance, Perfume, Essential Oils, lavender, peppermint, and tea tree oils, Extracts, Rose, Vanilla, Juniper or Mint extracts. Antimicrobial compounds are described in U.S. Pat. Nos. 6,709,647; 6,503,490; 5,885,562 are each incorporated in their entirety herein.

The various vitamins, moisturizers, skin conditioning agents, film forming polymers, botanicals, antioxidants, anti-perspirants, anti-dandruff and deodorants of the foregoing embodiments of the active gelled delivery systems, may be combined as a particular embodiment of an active emulsified delivery system.

In certain embodiments of the active emulsified delivery system, the rheology modifier is an organoclay. Various organoclays may be used in the active emulsified delivery system. In certain embodiments, the organoclay is a smectite clay exchanged with a quaternary ammonium cation having a formula of $[N-R^1R^2R^3R^4]^+$ wherein wherein $R^1$ comprises a group selected from (i) linear or branched aliphatic, aralkyl, or aromatic hydrocarbon groups having from 8 to 30 carbon atoms or (ii) alkyl or alkyl-ester groups having 8 to 30 carbon atoms; $R^2$, $R^3$ and $R^4$ are independently selected from the group consisting of (a) linear or branched aliphatic, aralkyl and aromatic groups having from 1 to about 30 carbon atoms. In certain such embodiments, the quaternary ammonium cation is selected from the group consisting of (i) dimethyldialkyl ammonium cation wherein the alkyl hydrocarbon group has 8 to 30 carbon atoms or 12 to 22 carbon atoms; (ii) benzyldimethylalkyl ammonium cation wherein the alkyl hydrocarbon group has 8 to 30 carbon atoms or 12 to 22 carbon atoms, and (iii) combinations thereof.

In certain other embodiments, the organoclay is an organically modified layered double hydroxide. These organically modified layered double hydroxides are comprised of layered double hydroxides and anionic surfactants. Layered double hydroxides (LDH) comprise an class of layered materials with positively charged hydroxide layers and charge balancing, mobile anions located in the interlayer region. The anions in the interlayers of LDHs are exchangeable. A variety of organic anionic surfactants can be intercalated between the hydroxide layers and suitable organic anions having at least 8 carbon atoms include mono-, di- or polycarboxylates, sulfonates, phosphonates, and sulfates. Organic anions in excess of the clay anion exchange capacity may optionally be co-intercalated as salts in the interlayer region. Layered double hydroxides are also known as mixed metal hydroxides and include the group of hydrotalcite materials. The layer charge density and organic surface treatment can be optimized to provide optimal properties with respect to rheological performance and other applications parameters. The disclosures of U.S. Pat. Nos. 7,968,740, 7,786,202, 6,479,421, 6,365,661, 6,028,023 and 3,539,306 as well as E.P. Patent No. 1,814,822 are each incorporated in their entirety herein.

In certain other embodiments of the active emulsified delivery system, the rheology modifier is selected from the group consisting of ethylcellulose, dibutyl lauroyl glutamide, dibutyl ethylhexanoyl glutamide, silica dimethyl silylate, hydrogenated styrene/isoprene copolymer, Polyamide-8, ethylene/propylene/styrene copolymer, butylene/ethylene/styrene copolymer, dextrin palmitate, trihydroxystearin and combinations thereof.

In certain embodiments of the active emulsified delivery system, the emollient is selected from the group consisting of hemisqualane, $C_{9-12}$ alkane, hemp oil, jojoba oil, caprylic/capric triglyceride, coco caprylate/caprate, octyldodecanol, natural oils, including plant oils, vegetable oils, and combinations thereof. In some such embodiments, the natural oil is sourced from plants, fruits, seeds, insects, or animals. In certain embodiments, the natural oil is selected from the group consisting of lanolin, shea butter, cocoa butter, mineral oil, beeswax, carnauba or palm wax, squalene, coconut oil, almond oil, olive oils and sesame oils. In certain embodiments, the natural emollient is an extract comprised largely of long chain waxy esters. It will be appreciated by a person skilled in the art that this list of natural oils is not an exhaustive list, and is representative only.

The present disclosure may be embodied in other specific forms without departing from the spirit or essential attributes of the invention. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed:

1. An active gelled delivery composition comprising:
   1 wt. % to 20 wt. % of a rheology modifier;
   50 wt. % to 90 wt. % of an emollient selected from the group consisting of hemisqualane, $C_{9-12}$ alkane, jojoba oil, caprylic/capric triglyceride, coco caprylate/caprate, octyldodecanol, and mixtures thereof; and
   wherein the rheology modifier is an organoclay, which is a smectite clay exchanged with a quaternary ammonium cation having the formula of $[N-R^1R^2R^3R^4]^+$, and
   wherein:
   $R^1$ is selected from the group consisting of linear aliphatic hydrocarbon groups having from 8 to 30 carbon atoms, branched aliphatic hydrocarbon groups having from 8 carbon atoms to 30 carbon atoms, aralkyl hydrocarbon groups having from 8 carbon atoms to 30 carbon atoms, aromatic hydrocarbon groups having from 8 carbon atoms to 30 carbon atoms, alkyl groups having 8 carbon atoms to 30 carbon atoms and alkyl-ester groups having 8 carbon atoms to 30 carbon atoms; and
   $R^2$, $R^3$ and $R^4$ are each selected from the group consisting of linear aliphatic groups having from 1 carbon atoms to about 30 carbon atoms, branched aliphatic groups having from 1 carbon atoms to about 30 carbon atoms, aralkyl groups having from 1 carbon atoms to about 30 carbon atoms and aromatic groups having from 1 carbon atoms to about 30 carbon atoms, wherein the quaternary ammonium cation is selected from the group consisting of dimethyldialkyl ammonium cation, benzyldimethylalkyl ammonium cation, and combinations thereof.

* * * * *